United States Patent
Carrara et al.

(10) Patent No.: US 9,827,407 B2
(45) Date of Patent: Nov. 28, 2017

(54) APPLICATOR SYSTEM FOR APPLYING A VISCOUS LIQUID TO THE HUMAN SKIN

(75) Inventors: Dario Carrara, Oberwil (CH); John Edward Burke, Cambridge (GB); David George Robinson, Cambridge (GB); Robert Peter Fernall, Saffron Walden (GB)

(73) Assignee: Ferring B.V., Hoofddorp (NL)

( * ) Notice: Subject to any disclaimer, the term of this patent is extended or adjusted under 35 U.S.C. 154(b) by 862 days.

(21) Appl. No.: 14/128,785

(22) PCT Filed: Jun. 20, 2012

(86) PCT No.: PCT/EP2012/061784
§ 371 (c)(1),
(2), (4) Date: Apr. 14, 2014

(87) PCT Pub. No.: WO2013/000778
PCT Pub. Date: Jan. 3, 2013

(65) Prior Publication Data
US 2014/0221943 A1      Aug. 7, 2014

Related U.S. Application Data

(60) Provisional application No. 61/501,292, filed on Jun. 27, 2011.

(30) Foreign Application Priority Data

Jun. 27, 2011   (EP) .................................... 11171533

(51) Int. Cl.
*A61M 35/00*      (2006.01)
*A61K 9/00*       (2006.01)
(Continued)

(52) U.S. Cl.
CPC ........... *A61M 35/003* (2013.01); *A45D 34/04* (2013.01); *A61K 9/0014* (2013.01); *A61K 9/06* (2013.01);
(Continued)

(58) Field of Classification Search
CPC ............................. A45D 34/04; A61M 35/003
See application file for complete search history.

(56) References Cited

U.S. PATENT DOCUMENTS 2,233,811 A    3/1941   Doty
5,772,347 A *  6/1998   Gueret ................. A45D 40/262
                                                401/175
(Continued)

FOREIGN PATENT DOCUMENTS

DE   10 2007 035202      1/2009
EP       0970650 A1      1/2000
(Continued)

OTHER PUBLICATIONS

"Modulus of Elasticity or Young's Modulus—and Tensile Modulus for common Materials," http://www.engineeringtoolbox.com/young-modulus-d_417.html, 6 pages, printed Oct. 10, 2016.*
(Continued)

*Primary Examiner* — Susan Su
(74) *Attorney, Agent, or Firm* — Finnegan, Henderson, Farabow, Garrett & Dunner LLP

(57) ABSTRACT

The application relates to an applicator system (1) for applying a viscous liquid, in particular a transdermal pharmaceutical formulation, to the human skin comprising a metering dispenser (2) in turn comprising a container holding the viscous liquid and a pump (5) for metering the liquid and an applicator (3) detachably connected to the dispenser (2) and comprising an application surface (6) for receiving
(Continued)

a metered amount of the liquid from the dispenser (2). The application surface (6) is convex.

25 Claims, 2 Drawing Sheets

(51) Int. Cl.
    *A61K 9/06*     (2006.01)
    *A61K 31/568*     (2006.01)
    *A61K 47/10*     (2017.01)
    *B65D 47/42*     (2006.01)
    *B65D 83/00*     (2006.01)
    *A45D 34/04*     (2006.01)

(52) U.S. Cl.
    CPC ............ *A61K 31/568* (2013.01); *A61K 47/10* (2013.01); *B65D 47/42* (2013.01); *B65D 83/00* (2013.01); *A45D 2200/056* (2013.01)

(56) References Cited

U.S. PATENT DOCUMENTS

| | | | | |
|---|---|---|---|---|
| 5,813,785 | A * | 9/1998 | Baudin | B65D 83/285 401/190 |
| 5,931,591 | A * | 8/1999 | McCracken | A45D 34/04 401/205 |
| 6,648,538 | B2 | 11/2003 | Gueret et al. | |
| 6,688,795 | B1 * | 2/2004 | Jacob | A45D 34/04 401/202 |
| 7,377,296 | B2 | 5/2008 | Gueret | |
| 2005/0054991 | A1 * | 3/2005 | Tobyn | B65D 83/0011 604/290 |
| 2006/0056905 | A1 * | 3/2006 | Thiebaut | A45D 34/04 401/207 |
| 2006/0153905 | A1 * | 7/2006 | Carrara | A61K 9/0014 424/449 |
| 2007/0000946 | A1 * | 1/2007 | Phipps | A61M 35/003 222/129.4 |
| 2007/0166361 | A1 | 7/2007 | Carrara et al. | |
| 2007/0186951 | A1 * | 8/2007 | Gueret | A45D 34/00 132/320 |
| 2007/0189841 | A1 * | 8/2007 | Gueret | A45D 40/262 401/266 |
| 2007/0258749 | A1 * | 11/2007 | Gueret | A45D 34/04 401/44 |
| 2010/0100060 | A1 | 4/2010 | Turner | |
| 2010/0168638 | A1 | 7/2010 | Korogi et al. | |
| 2010/0217176 | A1 * | 8/2010 | Carrara | A45D 34/04 604/20 |
| 2012/0004204 | A1 * | 1/2012 | Simes | A61K 9/0014 514/175 |
| 2012/0046264 | A1 * | 2/2012 | Simes | A61K 31/565 514/180 |
| 2014/0221945 | A1 * | 8/2014 | Dos Santos | A61M 35/003 604/311 |
| 2014/0270897 | A1 * | 9/2014 | Laurusonis | B05C 1/00 401/146 |
| 2015/0157839 | A1 * | 6/2015 | Bansal | A61M 35/003 604/290 |

FOREIGN PATENT DOCUMENTS

| | | |
|---|---|---|
| EP | 1 514 492 | 3/2005 |
| JP | U-H02-108778 | 8/1990 |
| JP | 2001263376 A | 3/2000 |
| JP | 2009-262946 | 11/2009 |
| WO | WO 00/03512 | 6/2000 |
| WO | WO 2004/080413 A2 | 9/2004 |
| WO | WO 2006/128255 | 12/2006 |
| WO | WO 2009/056819 A2 | 7/2009 |

OTHER PUBLICATIONS

"Materials Data Book," Cambridge University Engineering Department, 2003 Edition.*
International Search Report dated Aug. 20, 2012, PCT/EP2012/061784.

* cited by examiner

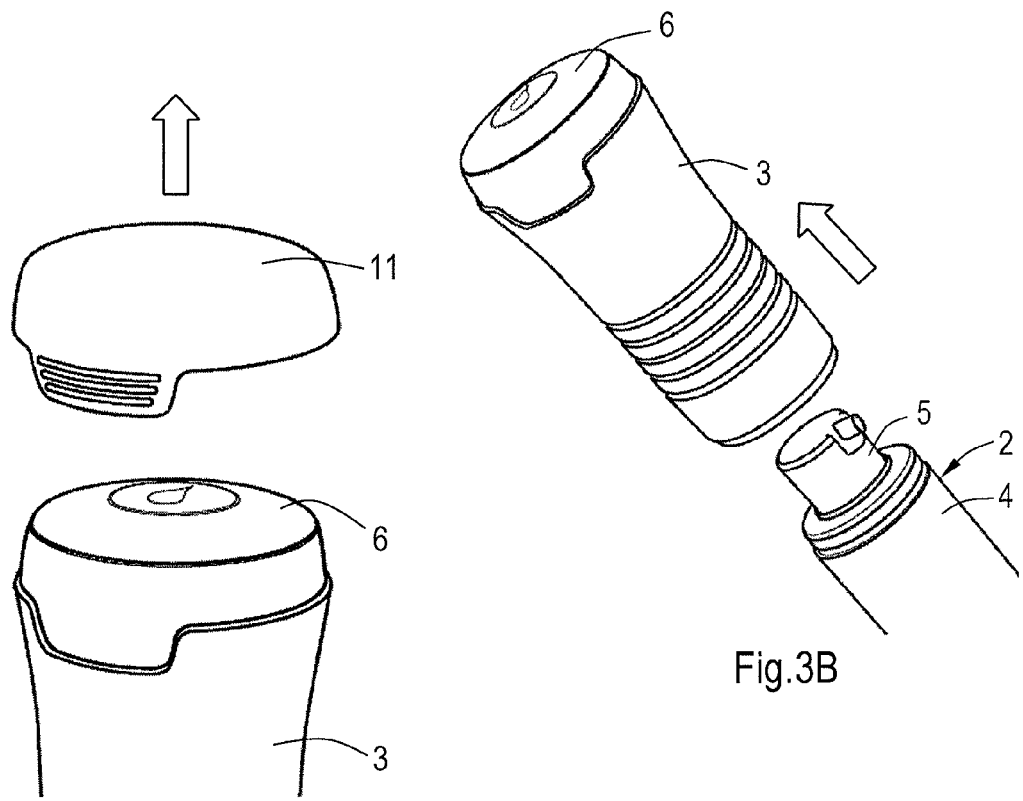
Fig.3A
Fig.3B
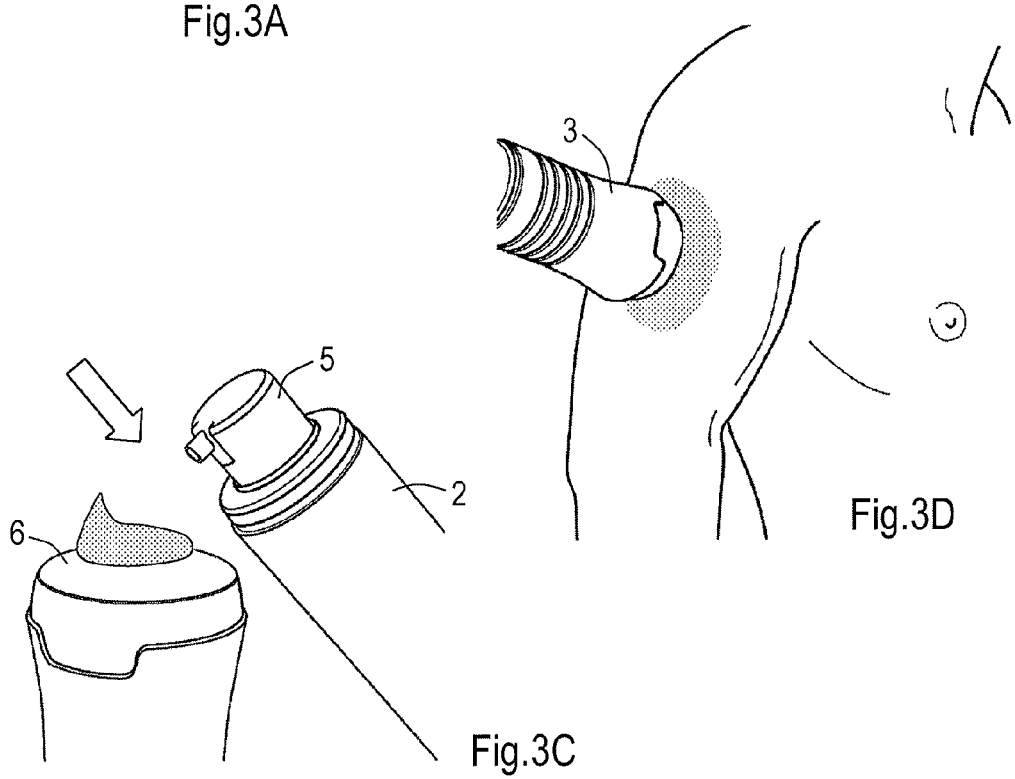
Fig.3C
Fig.3D

APPLICATOR SYSTEM FOR APPLYING A VISCOUS LIQUID TO THE HUMAN SKIN

CROSS REFERENCE TO RELATED APPLICATIONS

This is a U.S. National Phase application under 35 U.S.C. §371 of International Patent Application No. PCT/EP2012/061784, filed Jun. 20, 2012, which published as WO2013/000778, which claims the priority of European Patent Application No. 11171533.0 filed on Jun. 27, 2011 and U.S. Patent Application No. 61/501,292 filed Jun. 27, 2011. The foregoing applications and WO2013/000778 are hereby incorporated by reference in their entirety.

The invention relates to an applicator system for applying a viscous liquid, in particular a transdermal pharmaceutical formulation, to the human skin comprising, a metering dispenser in turn comprising a container holding the viscous liquid and a pump for metering the liquid and an applicator detachably connected to the dispenser and comprising an application surface for receiving a metered amount (dose) of the liquid from the dispenser.

As explained in WO 2008/083423, topical liquids such as sunscreens or medicated liquids have previously been provided in squeezable containers or in containers with a finger operated pump whereby a portion of the liquid is deposited on the treatment surface or on a free hand for subsequent application to the treatment surface. In either case the liquid is spread over the treatment surface with the free hand which results in the liquid being applied to a surface other than the treatment surface. It is not always acceptable for the free hand to be treated with a medicated liquid as the volume dispensed from the container may be a prescribed dose. This is particularly the case where the liquid is intended to have a therapeutic effect at the prescribed dose.

It is often desirable to provide an implement which temporarily retains the liquid for application to the treatment surface. Implements tend to suffer from the tension between temporarily retaining the liquid and having to release the liquid onto the treatment surface. Implements such as brushes and sponges are effective in spreading the liquid over the treatment surface however they tend to retain a volume of residual liquid after the application of the implement to the treatment surface. The retained volume may vary from application to application and as such it is difficult to accurately apply a metered dose to a treatment surface using an implement such as a brush or sponge.

In WO 2008/083423, it is considered desirable to provide an implement that is capable of applying a liquid to a treatment surface while minimising retention of residual liquid, and also an implement that was easy to clean after use. In WO 2008/083423, there is provided an implement for applying a volume of liquid to a treatment surface including a support means onto which is mounted a receptacle defining a reservoir space which receives the volume of liquid, the receptacle having a base and a wall. The wall is substantially transverse to the base and has a working surface that is used to spread the liquid over the treatment surface. At least the wall is resiliently deformable so in use the working surface maintains contact with the treatment surface when spreading the liquid.

The applicator according to WO 2008/083423 is intended for applying low viscosity liquids, typically having a viscosity of "less than 300 centipoise and often about 150 centipoise".

It is an object of the present invention to provide an improved applicator system that allows accurate transfer of metered amounts of viscous liquids, e.g. gels, from the application surface to the skin.

To this end, in the applicator system according to the present invention, the application surface is convex.

In an embodiment, the entire application surface is convex. In another embodiment, the application surface is continuous and in particular comprises no apertures or porous regions for metering the liquid to the surface from a supply within.

In a further embodiment, the application surface is rigid, i.e. non-deformable. More specifically, it is preferred that the material forming the surface has a Young's modulus of at least 1.5 GPa, preferably in a range from 2 to 4 GPa.

The application surface according to the present invention enables substantially complete transfer of the metered viscous liquid to the skin.

To further enhance transfer of the viscous liquid from the application surface to the skin, it is preferred that the application surface is smooth, preferably having a texture of stage 21 (measured in accordance with the VDI 3400 standard) or smoother.

The applicator according to the present invention can be used in combination with standard metering pumps, made in large quantities and thus providing good accuracy at relatively low costs. As the applicator surface provides substantially complete transfer of metered viscous liquid, the accuracy of the metering pump is extended to actual application.

In an embodiment, the dispenser has a metering accuracy of +/−15%, preferably +/−10% of the set amount and/or is configured to provide a metered amount per dispense in a range from 0.5 to 2.5 ml. In one embodiment, the dispenser provides a metered amount per dispense in a range from 1.0 to 2.0 ml. In another embodiment, the dispenser provides a metered amount per dispense of 1.25 ml.

In a particularly practical embodiment, the applicator doubles as a cap for the dispenser and/or comprises a sleeve to receive and secure the dispenser, e.g. through clamping or by means of a screwed or bayonet connection.

In a further embodiment, the applicator has a total length of at least 6.5 centimeters, preferably at least 9 centimeters, and is preferably not longer than 15 centimeters and/or at least 50% of the length of the applicator is suitable as a grip. Thus, the applicator is sufficiently long to envelop and secure the dispenser and to allow effective and comfortable handling by a user. In one embodiment, the applicator has a total length of about 12 centimeters.

In another embodiment, the dispenser contains a viscous liquid having a viscosity of at least 3000 centipoise (at 25° C.), preferably in a range from 5000 to 50000 centipoise, more preferably in a range from 17000 to 24000 centipoise. Thus, the viscous liquid, e.g. a gel, will adhere to the application surface, reducing the risk of gel metered onto the surface falling off e.g. as a result of movements by the user.

The system is especially suitable for applying a viscous liquid comprising testosterone or a derivative thereof.

When referring to testosterone, it should be understood to refer to the androgen steroidal hormone 17-β-hydroxyandrostenone also named (8R,9S,10R,13S,14S,17S)-17-hydroxy-10,13-dimethyl-1,2,6,7,8,9,11,12,14,15,16,17 dodecahydrocyclopenta[α]phenanthren-3-one (CAS Registry Number 58-22-0).

Examples of other androgens which may be administered with the applicator system of the invention include, but are not limited to, any esters of testosterone (such as testosterone enanthate, propionate, cypionate, phenylacetate, acetate, isobutyrate, buciclate, heptanoate, decanoate, undecanoate, caprate and isocaproate esters), 4-dihydrotestosterone, and any pharmaceutically acceptable derivatives of testosterone such as for example methyl testosterone, testolactone, oxymetholone and fluoxymesterone. These androgens may be used alone or in combinations of two or more thereof.

The system is also suitable for applying transdermal pharmaceutical formulations comprising at least one active agent and a solvent system present in an amount sufficient to solubilize the at least one active ingredient.

In one embodiment, the viscous liquid is a formulation comprising an active agent and a solvent system as specified in U.S. Pat. No. 7,198,801. In a specific embodiment, the active agent in the formulation is testosterone or a derivative thereof.

Examples of preferred testosterone formulations to be administered with an applicator of the invention are specified in PCT application no. PCT/EP2012/050695.

In one embodiment, the viscous liquid is a formulation comprising a C2-C4 alkanol in an amount between about 5-50% wt, polyalcohol in an amount between about 1-30% wt, monoalkyl ether of diethylene glycol in an amount between about 0.2-25% wt, gelling agent in an amount between about 0.05-4% wt, neutralizing agent in an amount between about 0.05-1% wt, and chelating agent in an amount between about 0.001-5.0% wt.

Unless expressly specified otherwise, the term "comprising" is used in the context of the present application to indicate that further members may optionally be present in addition to the members explicitly mentioned. It is, however, contemplated as a specific embodiment of the present invention that the term "comprising" encompasses the possibility of no further members being present. In other words, for the purpose of this embodiment, "comprising" is to be understood as having the meaning of "consisting of".

The following detailed description discloses specific and/or preferred variants of the individual features of the invention. The present invention also contemplates as particularly preferred embodiments those embodiments, which are generated by combining two or more of the specific and/or preferred variants described for two or more of the features of the present invention.

Unless expressly specified otherwise, all indications of relative amounts in the present application are made on a weight/weight basis. Indications of relative amounts of a component characterized by a generic term are intended to refer to the total amount of all specific variants or members covered by said generic term. If a certain component defined by a generic term is specified to be present in a certain relative amount, and if this component is further characterized to be a specific variant or member covered by the generic term, it is intended that no other variants or members covered by the generic term are additionally present such that the total relative amount of components covered by the generic term exceeds the specified relative amount, more preferably, in such case, no other variants or members covered by the generic term are present at all.

The term "C2 to C4 alkanol" as used herein should be understood to encompass one or more C2 to C4 alkanes substituted with a hydroxy group (—OH). In one embodiment, an alkanol comprised in a formulation to be administered by an applicator of the invention is one or more selected from the group consisting of ethanol, isopropanol and n-propanol. In another embodiment said alkanol is ethanol. In a further embodiment, said alkanol is ethanol present in an amount of about 44.0% wt.

The term "polyalcohol" as used herein should be understood to encompass one or more of a C2 to C6 alkane or C2 to C6 alkene, substituted with two or more hydroxy groups.

In some embodiments, a polyalcohol comprised in a formulation to be administered by an applicator of the invention is one or more selected from the group consisting of ethylene glycol, propylene glycol, butylene glycol, and hexylene glycol. In one embodiment the polyalcohol is propylene glycol. In another embodiment the polyalcohol is propylene glycol present in an amount of about 20.0% wt.

The term "monoalkyl ether of diethylene glycol" as used herein should be understood to encompass one or more diethylene glycols substituted with a C1 to C6 alkyl ether.

In one embodiment, monoalkyl ether of diethylene glycol comprised in a formulation to be administered by an applicator of the invention is one or both of diethylene glycol monoethyl ether (DGME) and diethylene glycol monomethyl ether. In another embodiment, the monoalkyl ether of diethylene glycol is diethylene glycol monoethyl ether. In yet another embodiment, said monoalkyl ether of diethylene glycol is diethylene glycol monoethyl ether in an amount of about 5.0% wt.

The term "gelling agent" as used herein should be understood to encompass any agent capable of altering the viscosity of a formulation. A gelling agent used in a formulation to be administered by an applicator of the invention can be one or more selected from the group including: carbomer, carboxyethylene or polyacrylic acid such as carbomer or carbopol 980NF (CARBOPOL™ 980 NF) or 940 NF, 981 or 941 NF, 1382 or 1342 NF, 5984 or 934 NF, ETD 2020, 2050, 934P NF, 971P NF, 974P NF, and Noveon AA-1 USP, cellulose derivatives such as ethylcellulose (EC), hydroxypropylmethylcellulose (HPMC), ethylhydroxyethylcellulose (EHEC), carboxymethylcellulose (CMC), hydroxypropylcellulose (HPC) (Klucel different grades), hydroxyethylcellulose (HEC) (Natrosol grades), HPMCP 55, and Methocel grades, natural gums such as arabic, xanthan, guar gums, and alginates, polyvinylpyrrolidone derivatives such as Kollidon grades, polyoxyethylene-polyoxypropylene copolymers such as Lutrol F grades 68 and 127, chitosan, polyvinyl alcohols, pectins, and veegum grades. A tertiary amine, such as triethanolamine or trolamine, can also be included in the formulation to thicken and neutralize the system.

In one embodiment, the gelling agent comprised in a formulation to be administered by an applicator of the invention is a carbomer. Carbomer relates to a class of homopolymers of acrylic acid with a high molecular weight, which are cross-linked with any of several polyalcohol allyl ethers. Non-limiting examples of carbomers are carbomer 940, carbomer 973, carbomer 980NF, carbomer C980NF (wherein the digit indicates the average molecular weight of the polymer chains). In a particular embodiment, the gelling agent comprised in a formulation to be administered by an applicator of the invention is carbomer C980NF. In yet another embodiment, the gelling agent is carbomer C980NF in an amount of 1.20% wt.

The term "neutralizing agent" as used herein should be understood to encompass one or more agents capable of neutralizing an acidic or basic component of a formulation to be administered by an applicator of the invention in order to achieve a stable and homogeneous formulation. Non-limiting examples of a neutralizing agent include:
diethylamine, diisopropylamine, a ternary amine such as triethanolamine or tromethamine,
tetrahydroxypropylethylendiamine, and alkalis such as KOH or NaOH solution.

In one embodiment, a neutralizing agent comprised in a formulation to be administered by an applicator of the invention is triethanolamine (also named trolamine interchangeably). In another embodiment, the neutralizing agent is triethanolamine in an amount of about 0.35% wt.

The term "chelating agent" as used herein should be understood to encompass one or more agents which complex and segregate residual traces of free multivalent cations susceptible to cause the physical degradation of a gel matrix (thereby causing loss of viscosity and breakdown of the formulation).

In one embodiment, a chelating agent comprised in a formulation to be administered by an applicator of the invention is edetate disodium. In a further embodiment, the chelating agent is edetate disodium in an amount of about 0.06% wt.

As used herein the term "solvent" may encompass any type of solvent suitable for use in transdermal formulations and may be the same or different from any other component of a formulation to be administered by an applicator of the invention, as detailed herein above. In one embodiment, a solvent comprised in a formulation to be administered by an applicator of the invention is water.

In one embodiment, a formulation to be administered by an applicator of the invention comprises 2% wt of testosterone, C2 to C4 alkanol, polyalcohol, and monoalkyl ether of diethylene glycol, wherein said formulation is substantially free of long-chain fatty alcohols, long-chain fatty acids, and long-chain fatty esters.

The omission of long chain fatty alcohols, long-chain fatty acids, and long-chain fatty esters provides formulations that do not have an unpleasant odor, irritation, and/or greasy texture caused by formulations that do include one or more of such compounds, resulting in greater patient compliance.

"Long-chain fatty alcohols, long-chain fatty acids, and long-chain fatty esters" as used herein should be understood to encompass fatty alcohols and fatty acids having a branched or linear carbon body having 8 or more carbon atoms, and esters thereof, i.e. fatty esters having a branched or linear acid moiety having 8 or more carbon atoms or having a branched or linear alcohol moiety having 8 or more carbon atoms.

"Substantially free of long-chain fatty alcohols, long-chain fatty acids, and long-chain fatty esters" as used herein should be understood to mean comprising fatty alcohols, fatty acids and/or fatty esters in a total amount of less than about 0.1% wt.

In one embodiment, a formulation to be administered by an applicator of the invention comprises 2% wt of testosterone, 44.0% wt of ethanol, 20.0% wt of propylene glycol, and 5.0% wt of diethylene glycol monoethyl ether, wherein said formulation is substantially free of long-chain fatty alcohols, long-chain fatty acids, and long-chain fatty esters.

In a further embodiment, a formulation to be administered by an applicator of the invention comprises 2% wt of testosterone, 44.0% wt of ethanol, 20.0% wt of propylene glycol, 5.0% wt of diethylene glycol monoethyl ether, 1.20% wt carbomer, 0.35% wt triethanolamine, 0.06% wt edetate disodium and water (q.s.) wherein said formulation is substantially free of long-chain fatty alcohols, long-chain fatty acids, and long-chain fatty esters.

In a further embodiment, a formulation to be administered by an applicator of the invention consists of 2% wt of testosterone, 44.0% wt of ethanol, 20.0% wt of propylene glycol, 5.0% wt of diethylene glycol monoethyl ether, 1.20% wt carbomer, 0.35% wt triethanolamine, 0.06% wt edetate disodium and water (q.s.).

In yet a further embodiment, a formulation to be administered by an applicator of the invention comprises 1% wt of testosterone, C2 to C4 alkanol, polyalcohol, and monoalkyl ether of diethylene glycol, wherein said formulation is substantially free of long-chain fatty alcohols, long-chain fatty acids, and long-chain fatty esters.

In another embodiment, a formulation to be administered by an applicator of the invention comprises 1% wt of testosterone, 44.0% wt of ethanol, 20.0% wt of propylene glycol, and 5.0% wt of diethylene glycol monoethyl ether, wherein said formulation is substantially free of long-chain fatty alcohols, long-chain fatty acids, and long-chain fatty esters.

In a further embodiment, a formulation to be administered by an applicator of the invention comprises 1% wt of testosterone, 44.0% wt of ethanol, 20.0% wt of propylene glycol, 5.0% wt of diethylene glycol monoethyl ether, 1.20% wt carbomer, 0.35% wt triethanolamine, 0.06% wt edetate disodium and water (q.s.) wherein said formulation is substantially free of long-chain fatty alcohols, long-chain fatty acids, and long-chain fatty esters.

In a further embodiment, a formulation to be administered by an applicator of the invention consists of 1% wt of testosterone, 44.0% wt of ethanol, 20.0% wt of propylene glycol, 5.0% wt of diethylene glycol monoethyl ether, 1.20% wt carbomer, 0.35% wt triethanolamine, 0.06% wt edetate disodium and water (q.s.).

In some embodiments, a formulation to be administered by an applicator system of the invention further comprises at least one of a buffering agent, moisturizing agent, humectant, surfactant, antioxidant, emollient, or buffer.

In a specific embodiment, the invention provides an applicator system to transdermally administer testosterone or a derivative thereof to a patient in need thereof, e.g. for use in the treatment of a disease or disorder associated with reduced endogenous testosterone production.

"Diseases and disorders associated with reduced endogenous testosterone production" should be understood to encompass any disease or disorder which is directly or indirectly related to a condition of a mammalian subject wherein the endogenous production of testosterone is either reduced or substantially non-existent or terminated. Diseases and disorders associated with reduced endogenous testosterone production relate to hormonal disorders such as, but not limited to, for example hypogonadism, female sexual disorder, hypoactive sexual disorder, and adrenal insufficiency.

A viscous liquid, in particular a transdermal pharmaceutical formulation, can be topically applied by an applicator system of the invention to any body part, such as, but not limited to, the chest, thigh, inner thigh, abdomen, shoulder, upper arm, upper torso, back, neck, feet, hands, axilla, or scrotum. In one embodiment, a formulation in the form of a gel is applied to an area of skin of from about 100 cm$^2$ up to about 1500 cm$^2$.

In a further aspect the invention provides a kit comprising at least one applicator system of the invention comprising a formulation comprising testosterone as detailed above, and instructions for use thereof. In an embodiment, the instructions include at least the steps that the applicator is to be removed from the dispenser, a dose of gel be metered onto the application surface, and the dose be applied onto the skin.

In one embodiment, a kit of the invention comprises an applicator system which is adapted for dispensing a predetermined measured amount of said testosterone formulation. In a specific embodiment, the predetermined amount is 1.25 ml per dispense.

In yet another specific embodiment, the applicator system of the invention dispenses 1.25 ml per dispense of a formulation consisting of 2% wt of testosterone, 44.0% wt of ethanol, 20.0% wt of propylene glycol, 5.0% wt of diethylene glycol monoethyl ether, 1.20% wt carbomer, 0.35% wt triethanolamine, 0.06% wt edetate disodium and water (q.s.).

To provide more insight in the background of the present invention, attention is drawn to the following patent publications.

US 2005/0054991 relates to a dosing device for topically administering a pharmaceutical formulation directly to the skin of a mammal. The device comprises a housing capable of storing at least one unit dose of a pharmaceutical formulation; an applicator adapted for topically administering a unit dose of the pharmaceutical formulation directly onto the skin; and an actuator capable of metering a single unit dose of the pharmaceutical formulation from a first position in which the unit dose is stored in the housing to a second position in which the single unit dose is external to the device on the applicator so that the single unit dose can be topically administered.

US 2007/0000946 relates to a dispenser for metered dosing of cream-based medicines comprising a barrel, a base having a threaded rod extending therefrom, a riser having at least one flexible seal which engages the barrel, and an applicator cap having apertures therein for spreading dispensed cream onto a user's skin.

EP 1 514 492 relates to a device for storing and dispensing a cosmetic product, comprising a unit refillable with a product delivered from a container. The refillable unit has an application unit, e.g. a sponge.

US 2007/0166361 relates to formulations for transdermal or transmucosal administration of an active agent such as estradiol.

WO 2009/064762 discloses a dispenser including a body defining a supply chamber therein for retaining a supply of a composition. The dispenser further includes an application portion having a front side with a concave application surface disposed externally and being sufficiently large to receive the skin of a patient for application of the composition thereto, and a conduit fluidly communicating the supply chamber with the application surface for delivering the composition to the application surface from the supply chamber.

WO 2006/005135 discloses a container including a receptacle (numeral 6 in the Figures of WO 2006/005135) for holding a substance, drug or liquid, and having an opening (7) to the receptacle (6) through which the substance can be dispensed and having a circular and domed spreading surface (15) adjacent the opening for spreading and the accurate delivery of a thin layer of liquid over an area of skin. In the embodiment shown in FIG. 15, the spreading surface (15) is of slightly convex form with radiused edges and circular shape. The receptacle (6) preferably holds between 50 µl to 500 µl of liquid having a viscosity of approximately 2.5 centipoises at an ambient temp of 20°.

WO 2007/140542 discloses an applicator (numeral 2 in the Figures of WO 2007/140542) for dispensing lotion from a dispensing device (1). The applicator includes a receptacle (13) for receiving a measured volume of lotion dispensed from the dispensing device (1). The receptacle (13) includes a collapsible reservoir space (15). Collapsing of the reservoir space (15) causes the lotion to pass through a passageway formed by apertures (18) in an outer member (14). An outer surface (21) of the outer member (14) provides a, preferably substantially convex, spreading surface for spreading the lotion on the treatment surface (20) of a user.

Within the framework of the present invention, the term "viscous liquid" includes, but is not limited to, gels, emulsions, creams, lotions and pastes.

The invention will now be explained in more detail with reference to the drawings, which schematically show a preferred embodiment according to the present invention.

FIGS. 3A to 3D illustrate steps of a method of applying a viscous liquid to the human skin.

Figure 1:
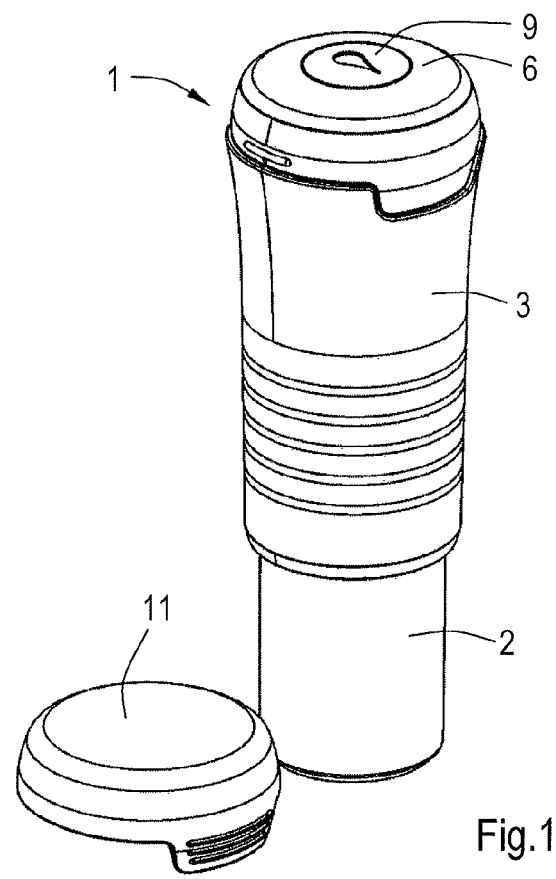
FIG. 1 is a perspective view of an applicator and dispenser according to the present invention.
Figure 2:
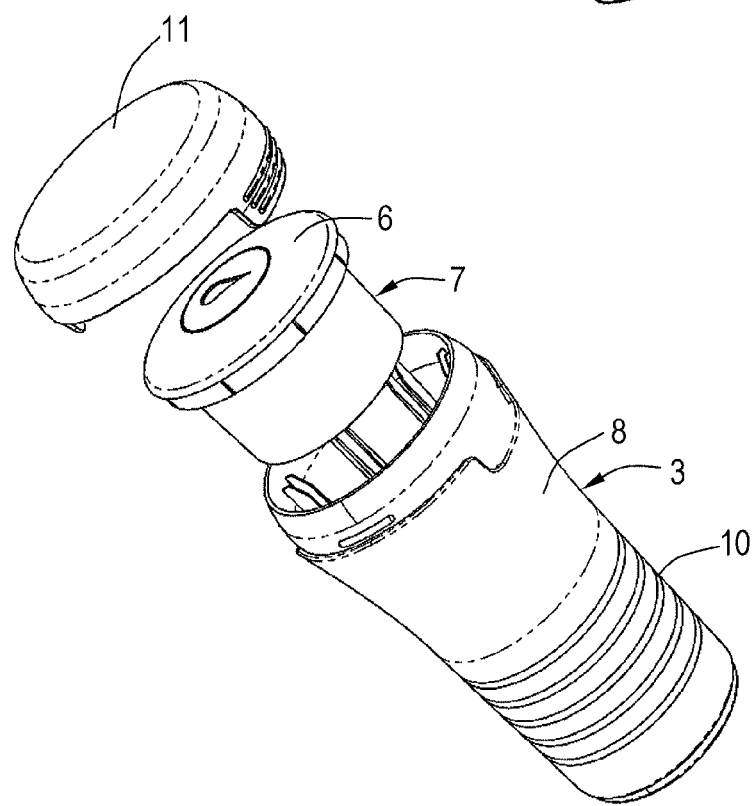
FIG. 2 is an exploded view of the applicator shown in FIG. 1.

FIGS. 1 and 2 show an applicator system 1 for applying a transdermal pharmaceutical formulation to the human skin, in accordance with the present invention. The system comprises a metering dispenser 2 and an applicator 3 clamped onto the dispenser.

The dispenser 2 is a so-called airless metering dispenser comprising a cylindrical housing 4 and a metering pump 5. The housing contains a pouch (not shown), e.g. made of an aluminium and polyethylene multilayer foil, to ensure protection of the liquid inside against oxygen and UV rays. The metering pump is actuated by pushing and delivers a constant and precise dose of, e.g. 1.25 ml+/−5% with each actuation. Suitable airless metering pumps are commercially available, e.g. from Lablabo.

The applicator comprises a convex, continuous application surface 6 for receiving a metered amount of the viscous liquid from the dispenser 2. In this example, the surface is part of an insert 7 which is clamp fitted and/or welded into the distal end of a sleeve 8. The insert is made of a plastomer, e.g. acrylonitrile butadiene styrene (ABS), having a Young's modulus of e.g. 3 GPa. The application surface is smooth, with a texture of stage 21 (measured in accordance with VDI 3400 standard) or smoother.

The surface 6 is provided with a symbol 9 to indicate the optimum location for metering the viscous liquid onto it. In this example, the symbol comprises a drop and a circle surrounding the drop to indicate the boundary of the optimum location.

As shown in FIG. 1, the applicator doubles as a cap for the dispenser. To this end, the sleeve 8, with its proximal end, fits clampingly about the dispenser 2.

In this example, the applicator has a length of 118 millimeters and approximately 90% of the length of the sleeve is provided with an elastomeric grip 10. The grip ends at some distance from the application surface to provide a barrier between the two.

To prevent any residues from rubbing off on other surfaces, e.g. towels or persons, such as family members of the user of the applicator system, a hygiene cap 11, made of e.g. polycarbonate, is provided to cover the application surface after use.

FIGS. 3A to 3D illustrate the typical steps of a method of applying a gel to the human skin with the present applicator. The hygiene cap is removed from the application surface (FIG. 3A) and the applicator is removed from the dispenser (FIG. 3B), in no specific order. A single dose of gel is metered onto the application surface (FIG. 3C) and the dose is applied onto the skin, preferably spreading the gel over a wider area (FIG. 3D) to facilitate uptake. If a double or triple amount is indicated, these latter two steps can be repeated accordingly.

The applicator system according to the present invention allows use of standard metering pumps, made in large quantities and thus providing good accuracy at relatively low costs, and enables substantially complete transfer of the amount of viscous liquid metered onto the application surface from that surface to the skin.

EXPERIMENTS

A phase 2, open-label, sequential dose escalation study in 18 adult hypogonadal males, i.e. males having a baseline morning serum testosterone concentration <300 ng/dL, was carried out to evaluate the pharmacokinetics of three volumes (1.25, 2.50 and 3.75 mL) of a testosterone gel formulation. The gel formulation consisted of 2% wt of testosterone, 44% wt of ethanol, 20.0% wt of propylene glycol, 5% wt of monoethyl ether of diethylene glycol, 1.20% wt of carbomer, 0.35% wt of triethanolamine, 0.06% wt of edetate disodium and water (hereinafter "the gel"). It was administered to the shoulder/upper arm either with the applicator shown in the Figures and described above or by hand application.

Objectives of the study in adult hypogonadal males were to:

1. investigate the steady-state pharmacokinetics of total testosterone (and dihydrotestosterone (DHT)) after 7 days of treatment with each of three volumes (1.25, 2.50 and 3.75 mL) of the gel applied with an applicator of the invention to the shoulder/upper arm;

2. investigate the steady-state pharmacokinetics of total testosterone (and DHT) after 7 days of treatment with one volume (2.50 mL) of the gel applied by hand to the shoulder/upper arm.

The gel, when administered by an applicator of the invention, was delivered in aliquots of 1.25 mL (23 mg/pump actuation). A total of 1.25 mL (23 mg, 1 pump actuation), 2.50 mL (46 mg, 2 pump actuations) or 3.75 mL (70 mg, 3 pump actuations) were administered per application.

Subjects applied 2.50 mL of the gel by hand for 7 days, followed by a 7-day washout period. After the washout, subjects applied three volumes of the gel (1.25, 2.50 and 3.75 mL) in a sequentially escalating fashion with an applicator of the invention, with no washout period between treatment phases (each seven days). Total testosterone and DHT blood levels were determined pre-application and at 2, 4, 6, 8, 10, 12 and 24 hours post-application on Visits 4 (2.50 mL, hand), 7 (1.25 mL, applicator), 9 (2.50 mL, applicator) and 11 (3.75 mL, applicator) for the determination of AUCτ (Area Under the Curve), Cmax (maximum concentration), Cavg (average concentration), and Estimated Responder Rate (percentage of patients having a concentration of total testosterone in the therapeutic range, 300 to 1050 ng/dL). The patient was also asked to state his preference for a particular method of application.

The duration of the treatment period for each subject from the screening visit to the last visit was approximately 70 days.

The results are shown in Tables 1 and 2 below.

TABLE 1

Different doses with applicator according to invention

| Treatment dose | AUCτ [ng · h/dL] (Mean ± SD) | $C_{ave}$ [ng/dL] (Mean ± SD) | $C_{max}$ [ng/dL] (Mean and range) |
|---|---|---|---|
| 1.25 mL | 5785 ± 1236 | 241 ± 52 | 398 225-690 |
| 2.50 mL | 7714 ± 2664 | 321 ± 111 | 641 233-1410 |
| 3.75 mL | 10353 ± 3820 | 431 ± 159 | 1025 215-3150 |

TABLE 2

Comparison application with applicator and by hand

| Treatment | AUCτ [ng · h/dL] (Mean ± SD) | $C_{avg}$ [ng/dL] (Mean ± SD) | $C_{max}$ [ng/dL] (Mean and range) | Estimated Responder Rate |
|---|---|---|---|---|
| 2.50 mL with applicator | 7714 ± 2664 | 321 ± 111 | 641 233-1410 | 55.6 |
| 2.50 mL by hand | 7829 ± 2759 | 326 ± 115 | 520 231-2020 | 50.0 |

Table 1 shows a substantially proportional increase of AUCτ, Cmax, and Cavg with increased dosage, confirming that the applicator provides accurate transfer of the metered amounts of the gel from the application surface to the skin. This proportionality can be employed to relatively quickly establish the correct dosage for a particular patient.

Table 2 shows a reduced variability of AUCτ, Cmax, and Cavg, when the gel is applied with the applicator instead of by hand. This too confirms more accurate transfer. Further, Table 2 shows a higher responder rate indicating an increased efficacy of the gel when it is applied with the applicator according to the present invention.

Also, 15 of the 18 subjects preferred use of the applicator over application by hand, i.e. the applicator provides an incentive for correct and efficacious administration of the gel.

The invention is not restricted to the above-described embodiments which can be varied in a number of ways within the scope of the claims.

The invention claimed is:

1. An applicator system for applying a transdermal pharmaceutical formulation, comprising:
    a metering dispenser comprising a container for holding a supply of the formulation and a pump for dispensing a metered amount of the formulation, wherein the formulation is in a form of a viscous liquid;

an applicator detachably connected to and enveloping the dispenser, wherein the applicator comprises a convex application surface for receiving a metered amount of the formulation from the dispenser, and the application surface is devoid of any aperture and porous region for metering the liquid to the application surface from the supply within; and a hygiene cap configured to cover the application surface.

2. The applicator system according to claim 1, wherein the application surface is rigid.

3. The applicator system according to claim 2, wherein the material forming the application surface has a Young's modulus of at least 1.5 GPa.

4. The applicator system according to claim 2, wherein the application surface is smooth.

5. The applicator system according to claim 1, wherein the dispenser has a metering accuracy of +/−15%, the dispenser dispenses the formulation in a range from 0.5 ml to 2.5 ml for each actuation, or both.

6. The applicator system according to claim 1, wherein the applicator doubles as a cap for the metering dispenser.

7. The applicator system according to claim 6, wherein the applicator comprises a sleeve to receive and secure the metering dispenser.

8. The applicator system according to claim 6, wherein the applicator has a total length of at least 6.5 centimeters, the applicator has at least 50% of the total length as a grip, or both.

9. The applicator system according to claim 1, wherein the application surface comprises a symbol, wherein the symbol marks an optimum location for placing the metered amount of the formulation onto the application surface.

10. The applicator system according to claim 1, wherein the viscous liquid has a viscosity of at least 3000 centipoise at 25 C.

11. The applicator system according to claim 1, wherein the formulation comprises at least one active agent and a solvent system present in an amount sufficient to solubilize the at least one active agent.

12. The applicator system according to claim 11, wherein the active agent is an androgen steroid hormone.

13. The applicator system according to claim 12, wherein the androgen steroid hormone is chosen from testosterone and a testosterone derivative.

14. The applicator system according to claim 13, wherein the testosterone is chosen from (8R,9S,10R,13S,14S,17S)-17-hydroxy-10,13-dimethyl-1,2,6,7,8,9,11,12,14,15,16,17 dodecahydrocyclopentaphenanthren-3-one, testosterone enanthate, testosterone propionate, testosterone cypionate, testosterone phenylacetate, testosterone acetate, testosterone isobutyrate, testosterone buciclate, testosterone heptanoate, testosterone decanoate, testosterone undecanoate, testosterone caprate, testosterone isocaprate, 4-dihydrotestosterone, and combinations thereof.

15. The applicator system according to claim 13, wherein the testosterone derivative is chosen from methyl testosterone, testolactone, oxymetholone, and fluoxymesterone.

16. The applicator system according to claim 11, wherein the formulation comprises a $C_2$ to $C_4$ alkanol in an amount from about 5-50% wt, a polyalcohol in an amount from about 1-30% wt, a permeation enhancer in an amount from about 0.2-25% wt, a gelling agent in an amount from about 0.05-4% wt, a neutralizing agent in an amount from about 0.05-1% wt, and a chelating agent in an amount from about 0.001-5.0% wt.

17. The applicator system according to claim 16, wherein the $C_2$ to $C_4$ alkanol is ethanol and the polyalcohol is propylene glycol.

18. The applicator system according to claim 16, wherein the formulation further comprises 1%-2% wt testosterone, and a monoalkyl ether of diethylene glycol, wherein the formulation is substantially free of long-chain fatty alcohols, long-chain fatty acids, and long-chain fatty esters.

19. The applicator system according to claim 18, wherein the monoalkyl ether of diethylene glycol is diethylene glycol monoethyl ether.

20. The applicator system according to claim 18, wherein the formulation comprises 2% wt testosterone.

21. The applicator system according to claim 11, wherein the formulation comprises 1% wt-2% wt testosterone, 44.0% wt ethanol, 20.0% wt propylene glycol, and 5.0% wt diethylene glycol monoethyl ether, wherein the formulation is substantially free of long-chain fatty alcohols, long-chain fatty acids, and long-chain fatty esters.

22. The applicator system according to claim 11, wherein the formulation comprises 1 wt-2% wt testosterone, 44.0% wt ethanol, 20.0% wt propylene glycol, 5.0% wt diethylene glycol monoethyl ether, 1.20% wt carbomer, 0.35% wt triethanolamine, 0.06% wt edetate disodium and water (q.s.), wherein the formulation is substantially free of long-chain fatty alcohols, long-chain fatty acids, and long-chain fatty esters.

23. The applicator system according to claim 22, wherein the formulation consists of 1% wt-2% wt testosterone, 44.0% wt ethanol, 20.0% wt propylene glycol, 5.0% wt diethylene glycol monoethyl ether, 1.20% wt carbomer, 0.35% wt triethanolamine, 0.06% wt edetate disodium and water (q.s.).

24. A kit comprising: (A) the applicator system according to claim 1, and (B) instructions for use thereof.

25. The kit according to claim 24, wherein the applicator system dispenses 1.25 ml of the formulation for each actuation of the metered dispenser, and wherein the dispensed formulation consists of 2% wt testosterone, 44.0% wt ethanol, 20.0% wt propylene glycol, 5.0% wt diethylene glycol monoethyl ether, 1.20% wt carbomer, 0.35% wt triethanolamine, 0.06% wt edetate disodium and water (q.s.).

* * * * *